US00PP29255P3

(12) United States Plant Patent
Braeunig

(10) Patent No.: US PP29,255 P3
(45) Date of Patent: Apr. 24, 2018

(54) ***IBERIS* PLANT NAMED 'FLORIBMOBI'**

(50) Latin Name: *Iberis sempervirens*
Varietal Denomination: Floribmobi

(71) Applicant: Florensis B.V., Hendrik-Ido-Ambacht (NL)

(72) Inventor: Tobias M. Braeunig, Quedlinburg (DE)

(73) Assignee: Florensis B.V., Hendrik-Ido-Ambacht (NL)

( * ) Notice: Subject to any disclaimer, the term of this patent is extended or adjusted under 35 U.S.C. 154(b) by 0 days.

(21) Appl. No.: 15/731,156

(22) Filed: Apr. 27, 2017

(65) Prior Publication Data

US 2017/0347515 P1 Nov. 30, 2017

Related U.S. Application Data

(60) Provisional application No. 62/392,271, filed on May 25, 2016.

(51) Int. Cl.
*A01H 5/02* (2018.01)

(52) U.S. Cl.
USPC ..... Plt./263.1
CPC ..... *A01H 5/02* (2013.01)

(58) Field of Classification Search
USPC ..... Plt./263.1
CPC ..... A01H 5/02
See application file for complete search history.

*Primary Examiner* — Kent L Bell
(74) *Attorney, Agent, or Firm* — Audrey Charles

(57) ABSTRACT

A new and distinct cultivar of *Iberis* plant named 'Floribmobi', characterized by its white-colored flowers, medium green-colored foliage, low vigor, and compact-mounded growth habit, is disclosed.

1 Drawing Sheet

Latin name of genus and species of plant claimed: *Iberis sempervirens.*

Variety denomination: 'Floribmobi'.

BACKGROUND OF THE INVENTION

The present invention relates to a new and distinct cultivar of *Iberis* plant botanically known as *Iberis sempervirens* and hereinafter referred to by the cultivar name 'Floribmobi'.

The new cultivar originated in a controlled breeding program in Quedlinburg, Germany during April 2013. The objective of the breeding program was the development of *Iberis* cultivars that flower early in the season and have a compact-mounded growth habit.

The new *Iberis* cultivar is the result of open-pollination. The female (seed) parent of the new cultivar is the proprietary *Iberis sempervirens* breeding selection coded 11420-2, not patented, characterized by its white-colored flowers, light green-colored foliage, and moderately vigorous, compact-mounded growth habit. The male (pollen) parent of the new cultivar is unknown. The new cultivar was discovered and selected as a single flowering plant within the progeny of the above stated open-pollination during April 2014 in a controlled environment in Quedlinburg, Germany.

Asexual reproduction of the new cultivar by terminal stem cuttings since April 2014 in Quedlinburg, Germany and Elburn, Ill. has demonstrated that the new cultivar reproduces true to type with all of the characteristics, as herein described, firmly fixed and retained through successive generations of such asexual propagation.

SUMMARY OF THE INVENTION

The following characteristics of the new cultivar have been repeatedly observed and can be used to distinguish 'Floribmobi' as a new and distinct cultivar of *Iberis* plant:

1. White-colored flowers;
2. Medium green-colored foliage;
3. Low vigor; and
4. Compact-mounded growth habit.

Plants of the new cultivar differ from plants of the female parent primarily in having darker green-colored leaves and a more compact growth habit.

Of the many commercially available *Iberis* cultivars, the most similar in comparison to the new cultivar is 'Fischbeck', not patented. However, in side by side comparisons, plants of the new cultivar differ from plants of 'Fischbeck' in at least the following characteristics:

1. Plants of the new cultivar have a darker leaf color than plants of 'Fischbeck'; and
2. Plants of the new cultivar have less growth vigor than plants of 'Fischbeck'.

BRIEF DESCRIPTION OF THE PHOTOGRAPHS

The accompanying photographs show, as nearly true as it is reasonably possible to make the same in color illustrations of this type, typical flower and foliage characteristics of the new cultivar. Colors in the photographs differ slightly from the color values cited in the detailed description, which accurately describes the colors of 'Floribmobi'. The plants were approximately 9-months old and grown in 17 cm containers in a poly-covered greenhouse in Amstelveen, The Netherlands. Plants were given one pinch at transplant.

DETAILED BOTANICAL DESCRIPTION

Figure 1:
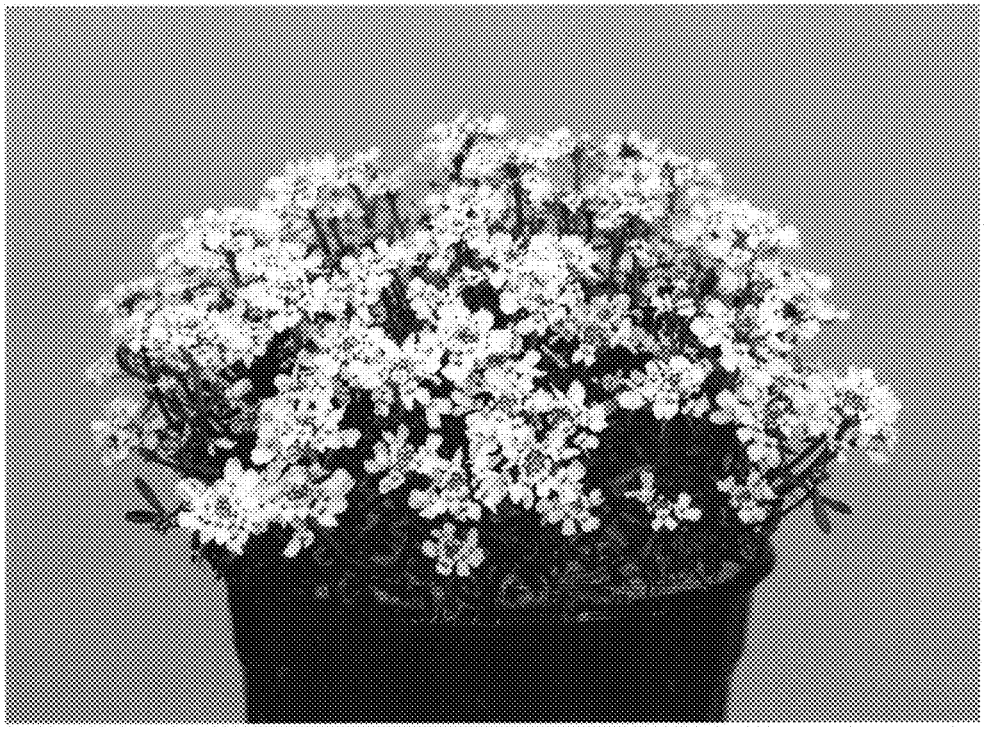
FIG. 1 illustrates a side view of the overall growth and flowering habit of 'Floribmobi'.
Figure 2:
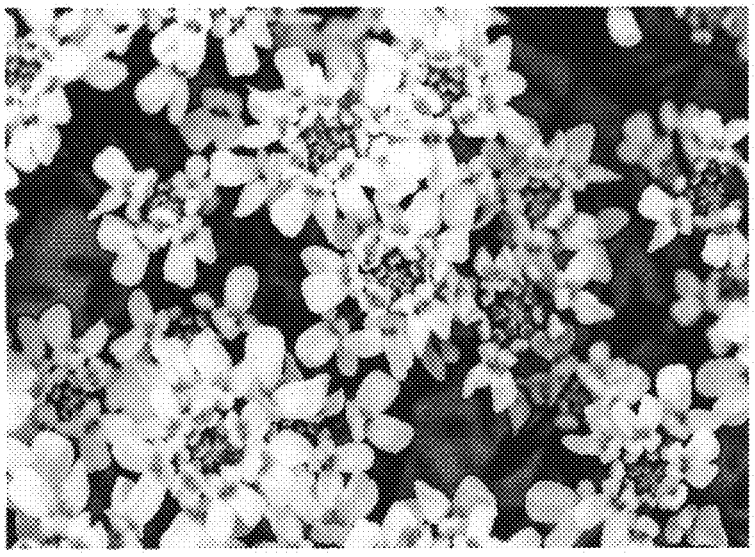
FIG. 2 illustrates a close-up view of the inflorescences of 'Floribmobi'.

The new cultivar has not been observed under all possible environmental conditions to date. Accordingly, it is possible that the phenotype may vary somewhat with variations in the environment, such as temperature, light intensity, and day length, without, however, any variance in genotype.

The chart used in the identification of colors described herein is The R.H.S. Colour Chart of The Royal Horticultural Society, London, England, 2015 edition, except where general color terms of ordinary significance are used. The color values were determined in March 2017 under natural light conditions in Boskoop, The Netherlands.

The following descriptions and measurements describe 9-month old plants produced from cuttings from stock plants and grown under conditions comparable to those used in commercial practice. The plants were grown utilizing a soilless growth medium in 17 cm containers in a poly-covered greenhouse in Amstelveen, The Netherlands. Plants were given one pinch at transplant. No supplemental heating or lighting was provided. Measurements and numerical values represent averages of typical plants.

Botanical classification: *Iberis sempervirens* cultivar Floribmobi.

Parentage:

*Female parent.*—Proprietary *Iberis sempervirens* breeding selection coded 11420-2, not patented.

*Male parent.*—Unknown.

Propagation:

*Type cutting.*—Terminal stem.

*Time to initiate roots.*—Approximately 12 to 14 days.

*Time to produce a rooted cutting.*—Approximately 35 to 42 days.

*Root description.*—Fine, fibrous.

*Rooting habit.*—Freely branching.

Plant description:

*Commercial crop time.*—Approximately 24 weeks from a rooted cutting to finish in a 15 cm pot, includes 6 to 7 weeks vernalization period.

*Growth habit and general appearance.*—Herbaceous perennial, low growth vigor, compact-mounded.

*Hardiness.*—USDA Zone 4a (−30° F. to −25° F.).

*Size.*—Height from soil level to top of plant plane: Approximately 13.3 cm. Width: Approximately 26.4 cm.

*Branching habit.*—Freely branching. Quantity of main branches per plant: Approximately 150.

*Branch.*—Shape: Rounded and slightly ribbed. Strength: Strong. Length to base of inflorescence: Approximately 7.3 cm. Diameter: Approximately 2.0 mm. Length of central internode: Approximately 1.5 mm. Texture: Glabrous. Color of young stems: 143C. Color of mature stems: 146B, stems become woody 199B to 199C with age.

Foliage description:

*General description.*—Quantity of leaves per main branch: Approximately 18. Fragrance: None. Form: Simple. Arrangement: Alternate.

*Leaves.*—Aspect: Perpendicular or obtuse angle to stem. Shape: Oblanceolate. Margin: Entire. Apex: Acute. Base: Attenuate, sessile. Venation pattern: Pinnate. Length of mature leaf: Approximately 1.7 cm. Width of mature leaf: Approximately 4.0 mm. Texture of upper and lower surfaces: Glabrous, leathery. Color of upper and lower surfaces of young foliage: 138A, venation indistinguishable. Color of upper surface of mature foliage: NN137A, midvein of 146C, other venation indistinguishable. Color of lower surface of mature foliage: 137B, midvein 144B to 144C, other venation indistinguishable.

Flowering description:

*Flowering habit.*—'Floribmobi' is freely flowering under outdoor growing conditions with substantially continuous blooming from early spring through summer.

*Lastingness of individual flower on the plant.*—Approximately 5 to 7 days.

Inflorescence description:

*General description.*—Type: Terminal corymb. Quantity per plant: Approximately 150. Fragrance: Moderate, pungent. Length or height: Approximately 3.0 cm. Width: Approximately 2.9 cm. Quantity of fully open flowers per corymb: Approximately 13.

*Peduncle.*—Strength: Strong. Aspect: Erect. Length: Approximately 2.6 cm. Diameter: Approximately 1.5 mm. Texture: Glabrous. Color: 144B.

Flower description:

*Type.*—Small, asymmetrical cruciferous flowers with a pair of two larger abaxial petals and a pair of two smaller adaxial petals, freely flowering, not persistent, facing outwardly to upright.

*Bud.*—Rate of opening: Generally takes 3 to 4 days for bud to progress from first color to fully open flower.

*Bud just before opening.*—Shape: Globose. Diameter: Approximately 2.0 mm. Color: Sepal centers of 144A and margins of 157D; petals of NN155C.

*Corolla.*—Shape: Cruciform lobes with claws surrounded by calyx. Aspect: Facing upward and outward. Length: Approximately 1.1 cm. Width: Approximately 1.2 cm.

*Petals.*—Quantity: 4. Shape: Obovate. Margin: Entire. Apex: Obtuse. Base: Attenuate. Length of abaxial lobe: Approximately 7.0 mm. Width of abaxial lobe: Approximately 5.0 mm. Length of adaxial lobe: Approximately 4.0 mm. Width of adaxial lobe: Approximately 3.0 mm. Length of claw of abaxial petal: Approximately 2.0 mm. Length of claw of adaxial petal: Approximately 1.0 mm. Width of claws: Less than 1.0 mm. Color of upper surface of lobe when first and fully open: NN155D. Color of lower surface of lobe when first and fully open: NN155D. Color of upper and lower surfaces of claws: NN155D with a midvein of 145A.

*Calyx.*—Shape: Cupped. Diameter: Approximately 3.0 mm.

*Sepals.*—Quantity per flower: 4, distinct. Shape: Ovate. Margin: Entire. Apex: Obtuse. Base: Truncate. Length: Approximately 3.0 mm. Width: Approximately 1.0 mm. Texture of inner and outer surfaces: Glabrous. Color of inner and outer surfaces: Centers of 143B and margins of 157D.

*Pedicel.*—Strength: Strong, flexible. Aspect: Acute angle to stem. Length: Approximately 7.0 mm. Diameter: Less than 1.0 mm. Texture: Glabrous. Color: 144B.

*Reproductive organs.*—Androecium: Stamen quantity: 6 per flower. Stamen length: Approximately 3.0 mm, 1 pair slightly shorter and inserted lower. Filament color: 145C. Anther shape: Sagittate, dorsifixed. Anther color: 12B. Pollen amount: Moderate. Pollen color: 4D. Gynoecium: Pistil quantity: 1 per flower, ovary superior, flattened orbicular. Pistil length: Approximately 2.0 mm. Stigma shape: Bifid. Stigma color: 145C. Style length: Approximately 1.0 mm. Style color: 143C. Ovary diameter: Approximately 1.0 mm. Ovary color: 143C.

Seed and fruit production: Neither seed nor fruit production has been observed.

Disease and pest resistance: Resistance to pathogens and pests common to *Iberis* has not been observed.

What is claimed is:

1. A new and distinct cultivar of *Iberis* plant named 'Floribmobi', substantially as herein illustrated and described.

* * * * *